US011598716B2

(12) United States Patent
Imade

(10) Patent No.: US 11,598,716 B2
(45) Date of Patent: Mar. 7, 2023

(54) GAS IMAGE DEVICE AND IMAGE ACQUISITION METHOD

(71) Applicant: KONICA MINOLTA, INC., Chiyoda-ku (JP)

(72) Inventor: Kyuichiro Imade, Chiyoda-ku (JP)

(73) Assignee: KONICA MINOLTA, INC., Tokyo (JP)

( * ) Notice: Subject to any disclaimer, the term of this patent is extended or adjusted under 35 U.S.C. 154(b) by 201 days.

(21) Appl. No.: 16/650,660

(22) PCT Filed: Jul. 12, 2018

(86) PCT No.: PCT/JP2018/026278
§ 371 (c)(1),
(2) Date: Mar. 25, 2020

(87) PCT Pub. No.: WO2019/064822
PCT Pub. Date: Apr. 4, 2019

(65) Prior Publication Data
US 2020/0309683 A1  Oct. 1, 2020

(30) Foreign Application Priority Data

Sep. 27, 2017  (JP) .............................. JP2017-186366

(51) Int. Cl.
*G01N 21/3504*  (2014.01)
*G01J 5/00*  (2022.01)
(Continued)

(52) U.S. Cl.
CPC ........ *G01N 21/3504* (2013.01); *G01J 5/0014* (2013.01); *G01N 1/24* (2013.01);
(Continued)

(58) Field of Classification Search
CPC .. G01N 21/3504; G01N 1/24; G01N 33/0009; G01N 33/0011; G01N 33/0031;
(Continued)

(56) References Cited

U.S. PATENT DOCUMENTS 5,001,346 A * 3/1991 Barkhoudarian .. G01N 21/3504
250/338.5
5,461,477 A * 10/1995 Marinelli ............. G01J 3/2823
356/333
(Continued)

FOREIGN PATENT DOCUMENTS

JP  5-281104  10/1993
JP  2004-208058  7/2004
(Continued)

OTHER PUBLICATIONS

Ren, Hsuan and Chang, Chein. Automatic spectral target recognition in hyperspectral imagery, Aerospace and Electronic Systems, IEEE Trans., 39: 4, 2003, pp. 1232-1249 (Year: 2003).*
(Continued)

*Primary Examiner* — Clayton E. LaBalle
*Assistant Examiner* — Kevin C Butler
(74) *Attorney, Agent, or Firm* — Cozen O'Connor

(57) ABSTRACT

This gas imaging device makes it possible to photograph gas without placing a burden on a user while enhancing the evidential reliability of imaging results. This gas imaging device comprises: an infrared imaging section for imaging, under a predetermined first photography condition, infrared radiation from a given area from which gas could leak; an image processing section for generating an image of the given area on the basis of output results from the infrared imaging section; and a control section for, on the basis of vicinity information for the given area and the output results of the infrared imaging section, calculating a reliability
(Continued)

indicating whether the first photography condition is suitable for photography of the gas and storing an image of the given area in a storage section in association with at least one from among the reliability and the vicinity information.

23 Claims, 6 Drawing Sheets

(51) Int. Cl.
  *H04N 5/33* (2006.01)
  *G01N 33/00* (2006.01)
  *G01N 1/24* (2006.01)
(52) U.S. Cl.
  CPC ..... *G01N 33/0009* (2013.01); *G01N 33/0011* (2013.01); *G01N 33/0016* (2013.01); *G01N 33/0031* (2013.01); *H04N 5/33* (2013.01); *G01J 2005/0077* (2013.01)
(58) Field of Classification Search
  CPC ................ G01N 33/0016; G01J 5/0014; G01J 2005/0077; H04N 5/33
  USPC ........................................................ 73/23.2
  See application file for complete search history.

(56) References Cited

U.S. PATENT DOCUMENTS

| | | | | |
|---|---|---|---|---|
| 6,985,233 | B2 * | 1/2006 | Tuschel | G01J 3/10 |
| | | | | 356/454 |
| 9,225,915 | B2 * | 12/2015 | Zeng | G01M 3/38 |
| 10,234,380 | B1 * | 3/2019 | Wang | G01N 21/3504 |
| 11,022,546 | B2 * | 6/2021 | Schmidt | H04N 5/33 |
| 2006/0220888 | A1 * | 10/2006 | Germouni | G08B 21/14 |
| | | | | 165/11.1 |
| 2010/0211333 | A1 * | 8/2010 | Pruet | G01J 3/027 |
| | | | | 356/519 |
| 2014/0008526 | A1 * | 1/2014 | Zeng | H04N 5/33 |
| | | | | 250/252.1 |
| 2015/0323449 | A1 * | 11/2015 | Jones | G01N 21/3103 |
| | | | | 356/437 |
| 2016/0097714 | A1 * | 4/2016 | Zeng | G01N 21/3504 |
| | | | | 250/338.5 |
| 2016/0203694 | A1 * | 7/2016 | Högasten | G08B 21/0476 |
| | | | | 348/164 |
| 2016/0238451 | A1 * | 8/2016 | Zeng | G01J 5/06 |
| 2016/0320296 | A1 * | 11/2016 | Asano | G01J 5/026 |
| 2017/0336281 | A1 * | 11/2017 | Waxman | G01N 21/3504 |
| 2018/0011009 | A1 * | 1/2018 | Sandsten | G01J 3/45 |
| 2018/0136072 | A1 * | 5/2018 | Cabib | G01M 3/04 |
| 2018/0188163 | A1 * | 7/2018 | Kester | G01M 3/38 |
| 2019/0113414 | A1 * | 4/2019 | Tsuzuki | G01M 3/04 |
| 2019/0145891 | A1 * | 5/2019 | Waxman | G01M 3/38 |
| | | | | 356/409 |
| 2019/0302013 | A1 * | 10/2019 | Wang | G01M 3/38 |
| 2019/0325587 | A1 * | 10/2019 | Asano | G01M 3/02 |
| 2019/0339159 | A1 * | 11/2019 | Israelsen | G01M 3/002 |
| 2019/0340914 | A1 * | 11/2019 | Israelsen | G08B 21/182 |
| 2020/0018693 | A1 * | 1/2020 | Akagawa | G01N 21/3504 |
| 2020/0025679 | A1 * | 1/2020 | Nygren | G01N 21/3504 |
| 2020/0059624 | A1 * | 2/2020 | Hirata | G01M 3/002 |
| 2020/0116583 | A1 * | 4/2020 | Hedberg | H04N 5/33 |
| 2020/0292445 | A1 * | 9/2020 | Morimoto | G08B 21/16 |
| 2020/0309683 | A1 * | 10/2020 | Imade | G01M 3/02 |
| 2020/0363327 | A1 * | 11/2020 | Cox | G01M 3/38 |
| 2021/0218909 | A1 * | 7/2021 | Schmidt | G01J 5/07 |
| 2022/0020141 | A1 * | 1/2022 | Vargas | G06T 11/001 |

FOREIGN PATENT DOCUMENTS

| | | |
|---|---|---|
| JP | 2013-210925 | 10/2013 |
| JP | 2016-097225 | 5/2016 |
| JP | 2017-90190 | 5/2017 |
| WO | WO 2015/166265 | 11/2015 |
| WO | WO-2015166265 A1 * | 11/2015 ............ G01J 5/0014 |
| WO | WO-2016139261 A1 * | 9/2016 ............ G01J 3/0208 |
| WO | WO 2017/073426 | 5/2017 |
| WO | WO 2017/073427 | 5/2017 |
| WO | WO-2018231735 A1 * | 12/2018 ............ G01J 5/0014 |

OTHER PUBLICATIONS

Prasad, S., Bruce, L. M. Decision Fusion With Confidence-Based Weight Assignment for Hyperspectral Target Recognition, Geoscience and Remote Sensing, IEEE Trans., 46: 5, 2008, pp. 1448-1456 (Year: 2008).*
International Search Report issued in corresponding Appln. No. WO 2019/064822.
Written Opinion dated Oct. 2, 2018 issued in International Patent Application No. PCT/JP2018/026278.
Office Action dated Aug. 16, 2022 issued in Japanese Patent Application No. 2019-544312.

* cited by examiner

| ITEM | NUMERICAL VALUE |
|---|---|
| OUTSIDE AIR TEMPERATURE | 24°C |
| WIND SPEED | 2m/s |
| DISTANCE | 10m |

|  | | | | | | | T1 |
|---|---|---|---|---|---|---|---|
| LARGE | 1 | 1 | 2 | 3 | 3 | 4 | |
| | 1 | 2 | 3 | 3 | 4 | 5 | |
| MEDIUM | 2 | 3 | 3 | 4 | 5 | ⑥ | |
| WIND SPEED | 3 | 3 | 4 | 5 | 6 | 6 | |
| SMALL | 3 | 4 | 5 | 6 | 6 | 7 | |
| | 4 | 5 | 6 | 6 | 7 | 7 | |

SMALL   MEDIUM   LARGE
ΔT

FIG. 4A

|  | | | | | | | T2 |
|---|---|---|---|---|---|---|---|
| FAR | 1 | 1 | 2 | 3 | 3 | 4 | |
| | 1 | 2 | 3 | 3 | 4 | 5 | |
| MEDIUM | 2 | 3 | 3 | 4 | 5 | 6 | |
| DISTANCE | 3 | 3 | 4 | 5 | 6 | 6 | |
| CLOSE | 3 | 4 | 5 | 6 | 6 | 7 | |
| | 4 | 5 | 6 | 6 | 7 | ⑦ | |

SMALL   MEDIUM   LARGE
ΔT

FIG. 4B

|  | | | | | | | T3 |
|---|---|---|---|---|---|---|---|
| LARGE | 4 | 3 | 3 | 2 | 1 | 1 | |
| | 5 | 4 | 3 | 3 | 2 | 1 | |
| MEDIUM | 6 | ⑤ | 4 | 3 | 3 | 2 | |
| WIND SPEED | 6 | 6 | 5 | 4 | 3 | 3 | |
| SMALL | 7 | 6 | 6 | 5 | 4 | 3 | |
| | 7 | 7 | 6 | 6 | 5 | 4 | |

CLOSE   MEDIUM   FAR
DISTANCE

FIG. 4C

| IMAGE PROCESSING CONDITION | IMAGE PROCESSING 1 | IMAGE PROCESSING 2 |
|---|---|---|
| | | |

FIG. 5A

| GAS TYPE | **** | **** | ... | **** |
|---|---|---|---|---|

FIG. 5B

| CONCENTRATION [%LEL·m] | ***** | ***** | ... | ***** |
|---|---|---|---|---|

FIG. 5C

GAS IMAGE DEVICE AND IMAGE ACQUISITION METHOD

RELATED APPLICATIONS

This is a U.S. National Phase Application under 35 USC 371 of International Application PCT/JP2018/026278 filed on Jul. 12, 2018.

This application claims the priority of Japanese application no. 2017-186366 filed Sep. 27, 2017, the entire content of which is hereby incorporated by reference.

TECHNICAL FIELD

The present invention relates to a gas imaging device and an image acquisition method.

BACKGROUND ART

In capturing images of gas using an infrared camera, environmental conditions such as measurement distance, wind speed, and background temperature will affect capturing conditions of the gas. Depending on the environmental conditions, some capturing conditions are not suitable for capturing images of the gas. In addition, it has been required that the user can learn which environment is suitable for capturing images of the gas.

The user cannot determine whether the peripheral environment is suitable for capturing images of the gas simply from captured images. To determine suitable conditions for capturing images of the gas, the user acquires environmental conditions using sensors and the like, and determines a reliability degree indicating whether the capturing conditions are suitable for capturing images of the gas by themselves, based on the environmental conditions.

CITATION LIST

Patent Literature

PTL 1: WO 2017/073426

SUMMARY OF INVENTION

Technical Problem

However, in the present situation for capturing images of the gas as described above, the user needs to determine the reliability degree based on the environmental conditions by themselves, which bothers the user. In addition, it is difficult for the user to determine the degree of influence in the actual process of capturing images of the gas. Furthermore, no link with imaging results has been demonstrated.

The present invention aims to provide a gas imaging device capable of capturing images of gas without bothering the user and an image acquisition method.

Solution to Problem

To achieve the object(s) mentioned above, a gas imaging device in the present invention comprises:
an infrared imaging section configured to image infrared rays from a target area where gas possibly leaks, using a first capturing condition determined in advance;
an image processing section configured to generate an image of the target area based on an output result from the infrared imaging section; and
a control section configured to calculate a reliability degree that indicates whether the first capturing condition is suitable for capturing an image of the gas based on peripheral information of the target area and the output result from the infrared imaging section and to control a storage section to store the image of the target area in association with at least one of the reliability degree and the peripheral information.

Further, an image acquisition method in the gas imaging device comprises:
imaging infrared rays from a target area where gas possibly leaks, using a capturing condition determined in advance;
generating an image of the target area based on a result of the imaging of the infrared rays; and
calculating a reliability degree that indicates whether the capturing condition is suitable for capturing an image of the gas based on peripheral information of the target area and the result of the imaging of the infrared rays, and storing the image of the target area in association with at least one of the reliability degree and the peripheral information.

Advantageous Effects of Invention

According to the present invention, reliability serving as evidence of imaging results can be increased and images of gas can be captured without bothering the user.

BRIEF DESCRIPTION OF DRAWINGS

FIG. 4A is an explanatory diagram of a table representing an example of a relation between a temperature difference, wind speed, and scores.

FIG. 4B is an explanatory diagram of a table representing an example of a relation between the temperature difference, a distance to the target area, and scores.

FIG. 4C is an explanatory diagram of a table representing an example of a relation between the distance to the target area, the wind speed, and scores.

FIG. 5A is a diagram illustrating an example of an image processing condition.

FIG. 5B is a diagram illustrating an example of a gas type.

FIG. 5C is a diagram illustrating an example of a gas concentration.

DESCRIPTION OF EMBODIMENTS

An embodiment of the present invention will be described below with reference to the accompanying drawings.

Figure 1:
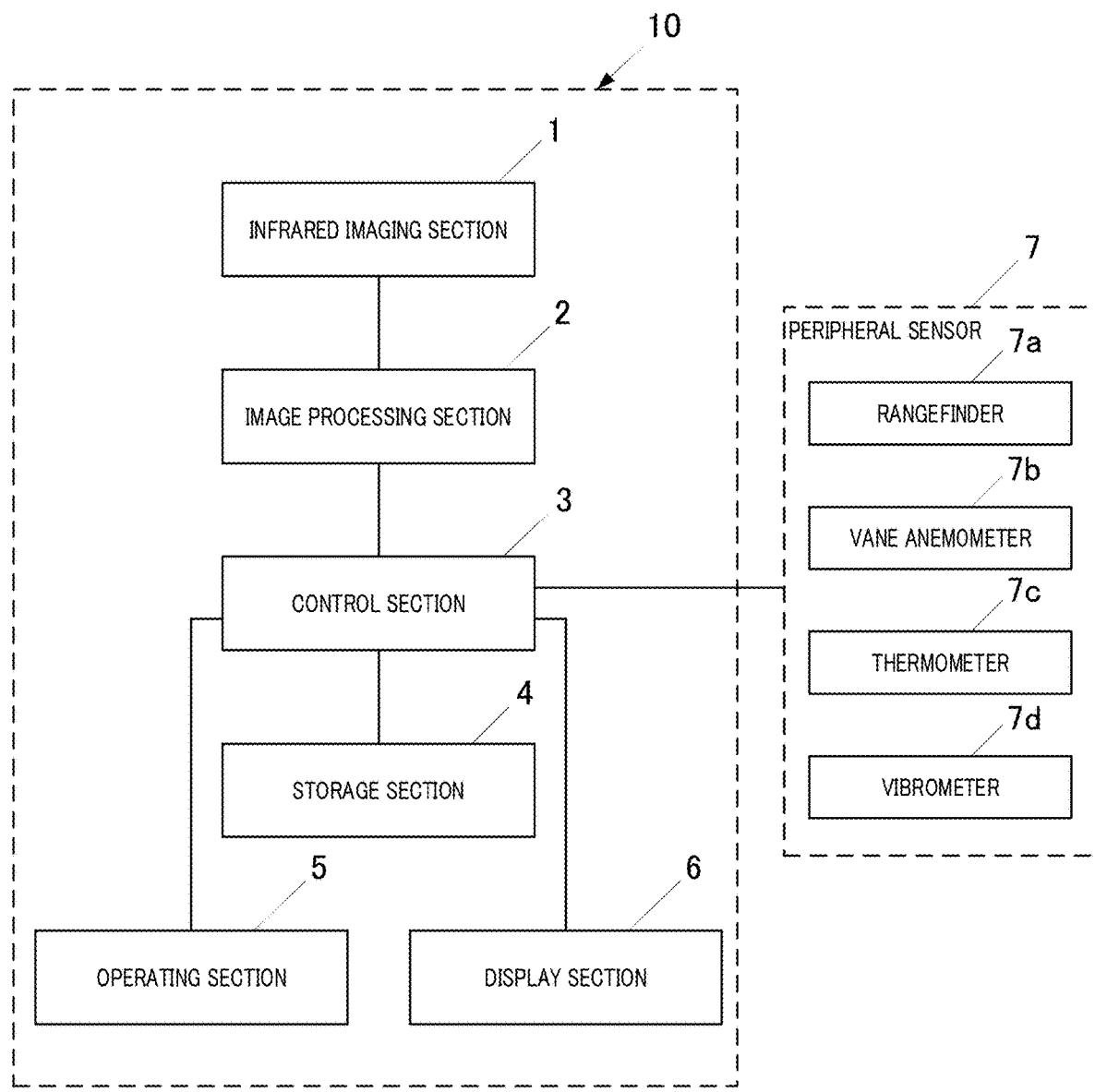
FIG. 1 is a block diagram illustrating a configuration of a gas imaging device in an embodiment of the present invention.

FIG. 1 is a block diagram illustrating a configuration of gas imaging device 10 in the embodiment.

Gas imaging device 10 in the present embodiment includes, as illustrated in FIG. 1, infrared imaging section 1, image processing section 2, control section 3, storage section 4, operating section 5, and display section 6. Gas imaging device 10 is connected to peripheral sensor 7 via interface such as a universal serial bus (USB). Image processing section 2 is implemented with a central processing unit (CPU), a read-only memory (ROM), a random access memory (RAM), a hard disk drive (HDD), and the like, and performs image processing of data. Control section 3 includes a CPU, a ROM, and a RAM. The CPU included in control section 3 reads a program corresponding to processing details from the ROM, loads the program into the RAM, and centrally controls operations in each block of gas imaging device 10 in cooperation with the loaded program.

Infrared imaging section 1 is connected to control section 3 and images infrared rays from a target area where the gas possibly leaks, using a first capturing condition determined in advance, under control of control section 3. Infrared imaging section 1 includes an imaging optical system (not illustrated) and an infrared image sensor (not illustrated), for example. The imaging optical system forms an infrared ray optical image of the target area on a predetermined image plane. The infrared image sensor is disposed with a light receiving surface coincident with the image plane and converts the infrared ray optical image of the target area into an electrical signal. The gas here may be any type of gas having a property of absorbing infrared rays, such as flammable gas, toxic gas, and vapor of an organic solvent.

Figures 2, 3:
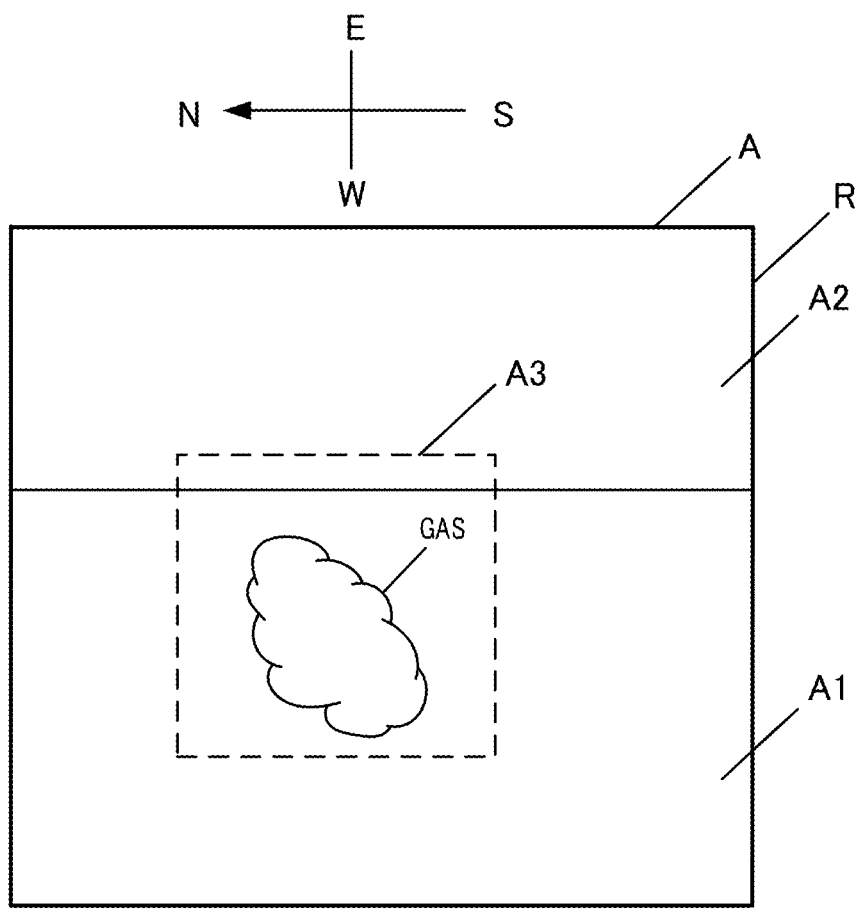
FIG. 2 is a diagram illustrating an example of a target area.
FIG. 3 is a diagram illustrating an example of peripheral information of the target area.

FIG. 2 is a diagram illustrating an example of a target area A. As illustrated in FIG. 2, the target area A in the present embodiment includes background A1, background A2, and specified area A3. Background A1 here is a land of asphalt pavement, and the difference between the temperature of background A1 and the outside air temperature is large. Background A2 here is a land of grass, and the difference between the temperature of background A2 and the outside air temperature is small In the present embodiment, the first capturing condition includes the distance between infrared imaging section 1 and target area A, a capturing angle of infrared imaging section 1, image range R in target area A, and specified area A3 specified by a user in target area A. The capturing angle of infrared imaging section 1 here corresponds to a direction of the optical axis of a lens that collects infrared rays. In the present embodiment, image range R coincides with target area A.

Image processing section 2 generates a heat distribution image (temperature information) of target area A through image processing of data that is output from the infrared image sensor. Specifically, the infrared image sensor measures infrared radiation energy radiated from target area A. Image processing section 2 converts the results measured by the infrared image sensor into the temperature of target area A by referring to a correlation between the infrared radiation energy (luminance information) and the temperature, and generates the heat distribution image (temperature information). Image processing section 2 performs visualization processing (extraction) of the gas from the infrared radiation energy (luminance information) measured by the infrared image sensor under the image processing condition determined in advance (refer to FIG. 5A). Image processing section 2 outputs an image of visualized gas in target area A (corresponding to the "image of the target area" of the present invention) to control section 3. If the reliability degree calculated based on the heat distribution image (temperature information) is low, image processing section 2 performs visualization processing of the gas from the infrared radiation energy (luminance information) under an image processing condition to increase the reliability degree.

Control section 3 controls display section 6 to display an image of target area A (image of visualized gas).

Peripheral sensor 7 includes rangefinder 7a, vane anemometer 7b, thermometer 7c, and vibrometer 7d, for example. Peripheral sensor 7 outputs measurement results from these meters to control section 3. Control section 3 acquires peripheral information of target area A based on the measurement results. In the present embodiment, the peripheral information of target area A includes the difference between the temperature of target area A and the outside air temperature, wind speed, wind direction, and the distance between infrared imaging section 1 and target area A. This distance may be hereinafter referred to as the "distance to target area A".

Rangefinder 7a is, for example, an optical, ultrasonic, or laser-light instrument that is connected to control section 3 and measures the distance to target area A under control of control section 3. Rangefinder 7a may also obtain, for example, the distance to the target area A based on facility design drawings illustrating arrangement positions of the infrared imaging section 1 and target area A.

Vane anemometer 7b is a device that is connected to control section 3 and measures the wind direction and the wind speed under control of control section 3. Vane anemometer 7b include a windmill (propeller) or ultrasonic instrument that measures the wind direction and the wind speed, for example.

Thermometer 7c is a device that is connected to control section 3 and measures the outside air temperature under control of control section 3. The outside air temperature here is, for example, the ambient air temperature of gas imaging device 10.

Vibrometer 7d is a device that is connected to control section 3 and measures the vibration state of gas imaging device 10 under control of control section 3. For vibrometer 7d, known instruments can be adopted, such as mechanical, magnetic, piezoelectric, optical, and electromagnetic instruments.

Operating section 5 is a device connected to control section 3 and is used for inputting, into control section 3, various commands such as a command to start the operation of imaging target area A, and various data required to image target area A such as an input of an identifier of specified area A3 specified by the user in target area A. Operating section 5 is, for example, a plurality of input switches to which predetermined functions are allocated, a keyboard, or a mouse. Note that operating section 5 may also be, for example, a device to input measurement results of peripheral sensor 7 as peripheral information of target area A (for example, the wind speed, the wind direction, and the distance to target area A). Accordingly, control section 3 also acquires the peripheral information of target area A through an input operation by the user using operating section 5.

Display section 6 is a device that is connected to control section 3 and outputs commands and data that are input from operating section 5, the heat distribution image, and the image of target area A (the image of visualized gas) under control of control section 3. Display section 6 is, for example, a display device such as a CRT display, an LCD, and an organic electroluminescence display. Note that a touch panel may be composed of operating section 5 and display section 6.

Storage section 4 is a circuit that is connected to control section 3 and stores various types of predetermined programs and various types of predetermined data under control of control section 3. Examples of the various types of predetermined programs include control processing programs such as an imaging program to image target area A. Storage section 4 include a read-only memory (ROM), which is a nonvolatile storage element, and an electrically erasable programmable ROM (EEPROM), which is a rewritable nonvolatile storage element, for example. Storage section 4 includes a random access memory (RAM) serving as what is called a working memory of control section 3 to store data and the like generated during execution of a predetermined program.

Control section 3 acquires peripheral information of target area A based on the measurement results of peripheral sensor 7. Examples of the peripheral information of target area A include the wind speed, the distance to target area A, the difference between the temperature of target area A and the outside air temperature, and the vibration state of infrared imaging section 1. The vibration state of infrared imaging section 1 is included in the peripheral information of target area A because the vibration of infrared imaging section 1 reduces gas detection accuracy and affects the reliability degree. Note that, in the present embodiment, the vibration state of infrared imaging section 1 is excluded from the peripheral information of target area A acquired by control section 3.

FIG. 3 is a diagram illustrating an example of the peripheral information of the target area A output from peripheral sensor 7. As illustrated in FIG. 3, the wind speed is 2 m/s. The distance to target area A is 10 m. The outside air temperature is 24° C. Note that the wind speed, the distance to target area A, and the outside air temperature each represent their representative values. In this context, the distance to target area A (representative value) is the distance from infrared imaging section 1 to a location where the gas can be generated. In the present embodiment, when the wind speed is classified into three levels, large, medium, and small, the wind speed 2 m/s is classified as the "medium" level. In addition, when the distance to the target area A is classified into three levels, far, medium, and close, the distance to target area A 10 m is classified as the "close" level.

Control section 3 acquires the heat distribution image (temperature information) of target area A. Control section 3 calculates a temperature difference $\Delta T$ between the temperature of target area A and the outside air temperature 24° C. based on the heat distribution image of target area A and an outside air temperature acquired in advance. Note that the temperature difference $\Delta T$ is calculated for each pixel of the heat distribution image. In the present embodiment, when the temperature difference $\Delta T$ is classified into three levels, large, medium, and small, the temperature difference $\Delta T$ is classified as the "large" level.

FIG. 4A is an explanatory diagram of table T1 representing an example of a relation between the temperature difference $\Delta T$, the wind speed, and numerical values. FIG. 4B is an explanatory diagram of table T2 representing an example of a relation between the temperature difference $\Delta T$, the distance to the target area A, and numerical values. FIG. 4C is an explanatory diagram of table T3 representing an example of a relation between the distance to target area A, the wind speed, and numerical values. The numerical values in tables T1, T2, and T3 correspond to parameters (the temperature difference $\Delta T$, the wind speed, and/or the distance to target area A). The minimum numerical value is 1 and the maximum numerical value is 7. Tables T1, T2, and T3 reveal that the numerical values increase as the temperature difference $\Delta T$ increases, as the wind speed decreases, and as the distance to target area A decreases.

Control section 3 obtains numerical value 6 by referring to table T1, based on the temperature difference $\Delta T$ classified as the "large" level and the wind speed classified as the "medium" level. Control section 3 also obtains numerical value 7 by referring to table T2, based on the temperature difference $\Delta T$ classified as the "large" level and the distance to target area A classified as the "close" level. Control section 3 also obtains numerical value 5 by referring to table T3, based on the distance to target area A classified as the "close" level and the wind speed classified as the "medium" level. Control section 3 obtains score 18 by summing up the above-described numerical values 6, 7, and 5.

As described above, control section 3 calculates the score by referring to tables T1, T2, and T3, based on the parameters (the temperature difference $\Delta T$, the wind speed, and/or the distance to target area A) and the heat distribution image. Note that the score is calculated for each pixel of the heat distribution image of target area A.

The capacity of gas absorbing infrared rays varies depending on the type or the concentration of the gas. To increase the reliability degree, the image processing condition corresponding to the gas type and the gas concentration is to be selected. However, some of the image processing conditions set as initial settings in gas imaging device 10 may fail to correspond to the gas type or the gas concentration. In the present embodiment, control section 3 selects the image processing condition corresponding to the gas type and the gas concentration to increase the reliability degree, and controls display section 6 to display the selected image processing condition. Note that the gas type here is set as an initial setting for gas imaging device 10. If the type of gas that possibly leaks in target area A is known, such gas type and the gas concentration may be input in advance into control section 3 before capturing images of the gas. The gas concentration is, for example, a concentration-thickness product of the gas, that is, a product of the gas concentration and the gas thickness. The image processing condition corresponds to, for example, the level of noise eliminated by the filter.

Generating the image of target area A (the image of visualized gas) based on the image processing condition corresponding to the above-described gas type and gas concentration will prevent reduction in the resolution and the like of the image of target area A. That is, the image processing conditions, the gas type, and the gas concentration are to be taken into account in calculating the reliability degree, which indicates whether the capturing condition is suitable for capturing images of the gas. For this reason, in the present embodiment, control section 3 multiplies the above-described score by a coefficient corresponding to at least one of the image processing condition (refer to FIG. 5A), the gas type (refer to FIG. 5B), and the gas concentration (refer to FIG. 5C). The control section 3 calculates the reliability degree based on the numerical value thus obtained. Note that the reliability degree is calculated for each pixel of the heat distribution image.

Control section 3 causes storage section 4 to store the image of target area A in association with the reliability degree and the peripheral information. Control section 3 controls display section 6 to display the image of target area A in association with the reliability degree.

Figure 6:
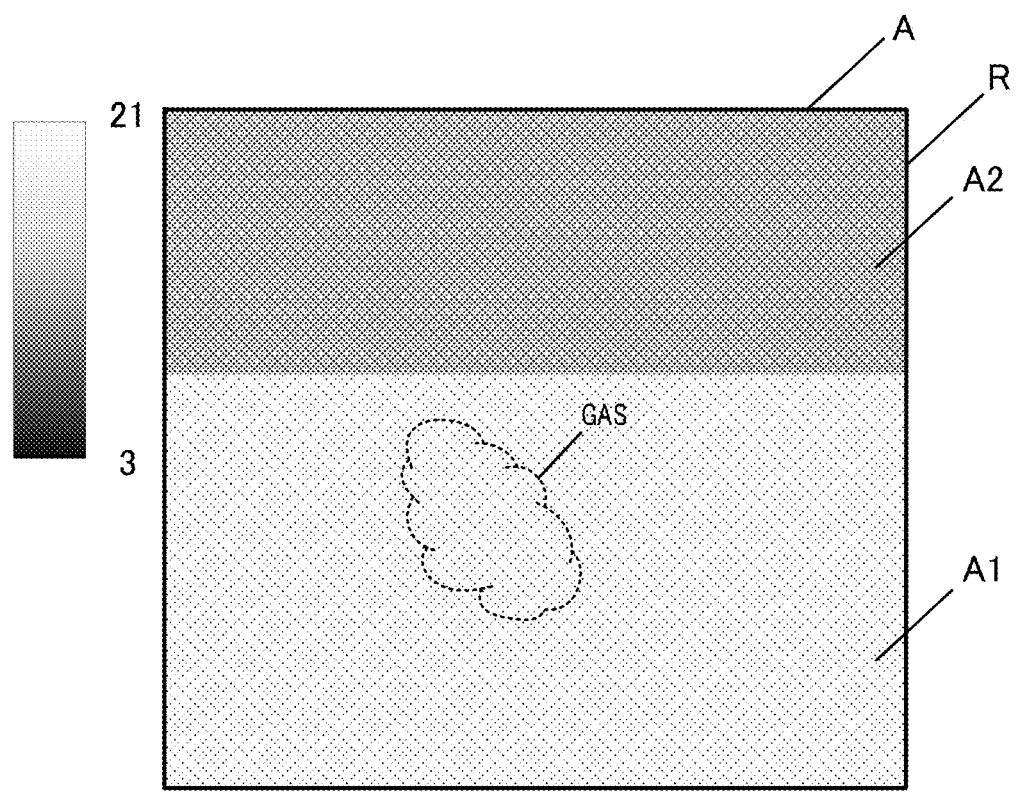
FIG. 6 is a diagram illustrating a heat distribution image associated with a reliability degree displayed on a display section.

FIG. 6 is a diagram illustrating a heat distribution image associated with the reliability degree displayed on display section 6. The description below will be made assuming that the score calculated by control section 3 referring to tables T1, T2, and T3 described above will not change after being multiplied by the coefficient corresponding to the image processing condition and the like. The reliability degree illustrated in FIG. 6 corresponds to any of the scores from 3 to 21. Control section 3 controls display section 6 to display the pixels from low to high reliability degrees for each pixel in the heat distribution image using 19-level gradation from score 3 to score 21 (density from dark to light). As illustrated in FIG. 6, the pixels representing background A1 are displayed relatively light, and it is thus found that the first capturing condition in background A1 has a relatively high reliability degree. In contrast, the pixels representing background A2 are displayed relatively dark, and it is thus found that the first capturing condition in the background A2 has a relatively low reliability degree.

Background A1 is, as illustrated in FIG. 2, the location where the gas possibly leaks. Because the first capturing condition in background A1 has a relatively high reliability degree, the necessity of changing the first capturing condition is low. However, if the first capturing condition in background A1 has a low reliability degree, the first capturing condition needs to be changed to increase the reliability degree.

In the present embodiment, control section 3 controls display section 6 to display a second capturing condition to increase the reliability degree. The second capturing condition here is the distance to the target area A and the capturing angle of the infrared imaging section 1. As is clear from tables T2 and T3 illustrated in FIGS. 4B and 4C, to increase the reliability degree, the distance to target area A is preferably as close as possible within the acceptable range. Additionally, to increase the reliability degree, the capturing angle of the infrared imaging section 1 is preferably an angle orthogonal to the wind direction so that the second capturing condition is not affected by wind. Control section 3 controls display section 6 to display the distance to target area A (distance as close as possible within the acceptable range) and the capturing angle of the infrared imaging section 1 (for example, an angle toward west), based on the distance to target area A and the wind direction (toward north as illustrated in FIG. 2).

Control section 3 controls display section 6 to display the image processing condition (for example, image processing 1 and 2 as illustrated in FIG. 5A) corresponding to the gas type and the gas concentration to increase the reliability degree. Specifically, the second capturing condition and the image processing condition are displayed in text or illustrated in a diagram.

Control section 3 causes storage section 4 to store an image of target area A in association with a captured date and time and a captured location.

Figure 7:
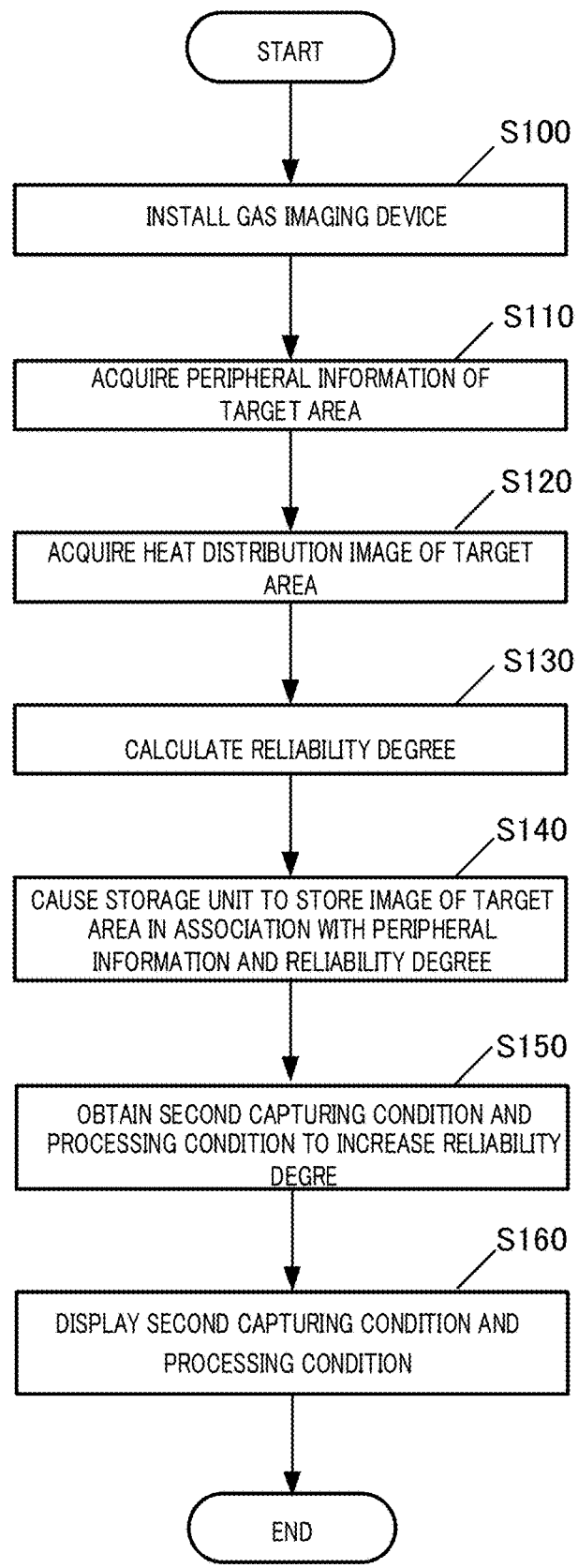
FIG. 7 is a flowchart illustrating a procedure of imaging the target area.

Next, a procedure of imaging target area A will be described referring to FIG. 7. FIG. 7 is a flowchart illustrating the procedure of imaging target area A.

Firstly, the user installs gas imaging device 10 on a location to observe target area A (Step S100).

At Step S110, control section 3 acquires peripheral information of target area A.

At Step S120, control section 3 acquires a heat distribution image of target area A.

At Step S130, control section 3 calculates a reliability degree based on the peripheral information of target area A and the heat distribution image of target area A.

At Step S140, control section 3 causes storage section 4 to store the image of target area A in association with the peripheral information of target area A and the reliability degree.

At Step S150, control section 3 obtains the second capturing condition and the image processing condition to increase the reliability degree.

At Step S160, control section 3 controls display section 6 to display the second capturing condition and the image processing condition.

Gas imaging device 10 according to the above-described embodiment includes infrared imaging section 1 configured to image infrared rays from the target area where gas possibly leaks using the first capturing condition determined in advance; image processing section 2 configured to generate the heat distribution image of target area A through image processing of data that is output from infrared imaging section 1; and control section 3 configured to calculate the reliability degree that indicates whether the first capturing condition is suitable for capturing images of gas based on the peripheral information and the heat distribution image of target area A, and cause storage section 4 to store the heat distribution image in association with the reliability degree and the peripheral information. This configuration allows the user to capture images of the gas without being bothered because the user does not have to determine the reliability degree by themselves.

In gas imaging device 10 according to the above-described embodiment, control section 3 obtains the second capturing condition and the image processing condition to increase the reliability degree and controls the display section 6 to display these conditions. This operation allows the user to set a more suitable second capturing condition and image processing condition.

In gas imaging device 10 according to the above-described embodiment, control section 3 calculates the reliability degree based on at least one of the image processing condition, the gas type, and the gas concentration. As described above, because the gas type and the gas concentration affect the resolution and the like of the image of target area A, they are to be taken into account in calculating the reliability degree. Calculating the reliability degree based on the gas type and the like can calculate the reliability degree more appropriately.

In gas imaging device 10 according to the above-described embodiment, control section 3 causes storage section 4 to store the image of target area A in association with the captured date and time and the captured location. This operation enables, for example, check of the image of target area A every predetermined time based on the captured date and time. This also achieves fixed-point observation of target area A based on the captured location.

In the above-described embodiment, control section 3 calculates the reliability degree based on the heat distribution image of target area A, and control section 3 controls display section 6 to display the second capturing condition to increase the reliability degree; however, the present invention is not limited thereto. If the user specifies specified area A3 (refer to FIG. 2), infrared imaging section 1 images specified area A3 and image processing section 2 generates the heat distribution image in specified area 3. In this case, control section 3 may also calculate the reliability degree based on the heat distribution image in specified area 3 and control display section 6 to display the second capturing condition to increase the reliability degree.

In the above-described embodiment, control section 3 causes the image of target area A to be stored in association with the reliability degree and the peripheral information of target area A; however, the present invention is not limited thereto. Control section 3 may cause the image of target area A to be stored in association with at least one of the reliability degree and the peripheral information of target area A.

In the above-described embodiment, control section 3 multiplies the score by the coefficient corresponding to at least one of the image processing condition, the gas type, and the gas concentration, and calculates the reliability degree based on the numerical value thus obtained; however, the present invention is not limited thereto. For example, a table may be provided that represents a relation between the reliability degree and at least one of the image processing condition, the gas type, and the gas concentration, and control section 3 may calculate the reliability degree by referring to the table.

In the above-described embodiment, control section 3 causes display section 6 to display the image of target area A in association with the reliability degree; however, the present invention is not limited thereto. For example, control section 3 may cause display section 6 to display the peripheral information of target area A. Control section 3 may also cause display section 6 to display the image of target area A in association with the peripheral information of target area A. This operation allows the user to recognize the peripheral information, whereby usability of gas imaging device 10 is increased.

In the above-described embodiment, peripheral sensor 7 is connected to gas imaging device 10 via an interface; however, the present invention is not limited thereto. For example, peripheral sensor 7 may be incorporated in gas imaging device 10.

The above-described embodiment is merely an example of specific implementation of the present invention, and the technical scope of the present invention should not be construed in a limiting sense. That is, the present invention can be embodied in a variety of forms without departing from its spirit or principal characteristics.

The entire disclosure of the specification, drawings, and abstract included in Japanese Patent Application No. 2017-186366, filed on Sep. 27, 2017 is incorporated herein by reference.

INDUSTRIAL APPLICABILITY

The present invention is suitably used for a gas imaging device that is required to increase reliability serving as evidence of imaging results and capture images of gas without bothering the user.

REFERENCE SIGNS LIST

1 Infrared imaging section
2 Image processing section
3 Control section
4 Storage section
5 Operating section
6 Display section
7 Peripheral sensor
7a Rangefinder
7b Vane anemometer
7c Thermometer
7d Vibrometer
10 Gas imaging device

The invention claimed is:

1. A gas imaging device, comprising:
an infrared imager configured to image infrared rays from a target area where gas possibly leaks, using a first capturing condition determined in advance;
a hardware processor configured to generate an image of the target area based on an output result from the infrared imager; and to calculate a reliability degree that indicates whether the first capturing condition is suitable for capturing an image of the gas based on peripheral information of the target area and the output result from the infrared imaging section and to control a storage device to store the image of the target area in association with at least one of the reliability degree and the peripheral information, and to cause a display device to display a second capturing condition to increase the reliability degree.

2. The gas imaging device according to claim 1, wherein the hardware processor causes a display device to display at least one of the reliability degree and the peripheral information.

3. The gas imaging device according to claim 2, wherein the display device displays the image of the target area.

4. The gas imaging device according to claim 1, wherein
the hardware processor performs image processing on the output result from the infrared, using an image processing condition determined in advance, and
causes a display device to display an image processing condition to increase the reliability degree.

5. The gas imaging device according to claim 1, wherein the first capturing condition includes a distance between the infrared imager and the target area.

6. The gas imaging device according to claim 1, wherein the first capturing condition includes a capturing angle of the infrared imager.

7. The gas imaging device according to claim 1, wherein the first capturing condition includes an image range of the target area.

8. The gas imaging device according to claim 1, wherein the first capturing condition includes an area specified by a user in the target area.

9. The gas imaging device according to claim 1, wherein the peripheral information includes a difference between temperature of the target area and outside air temperature.

10. The gas imaging device according to claim 9, wherein the peripheral information is information input through an input operation by a user.

11. The gas imaging device according to claim 9, wherein the peripheral information is information acquired by a sensor.

12. The gas imaging device according to claim 1, wherein the peripheral information includes at least one of wind speed, wind direction, a distance between the infrared imager and the target area, and a vibration state of the infrared imager.

13. The gas imaging device according to claim 1, wherein the hardware processor further calculates the reliability degree based on at least one of an image processing condition, a gas type, and a gas concentration.

14. The gas imaging device according to claim 13, further comprising a table that represents a relation between the reliability degree and at least one of the image processing condition, the gas type, and the gas concentration, wherein
the hardware processor calculates the reliability degree with reference to the table.

15. The gas imaging device according to claim 1, wherein the hardware processor causes the storage device to store the image of the target area in association with at least one of a captured date and time and a captured location.

16. The gas imaging device according to claim 1, wherein the image of the target area is a heat distribution image; and the hardware processor is configured to calculate the reliability degree for each pixel of the heat distribution image based on peripheral information of the target area and the heat distribution image, and control the storage device to store the heat distribution image as the image of the target area.

17. An image acquisition method, comprising:

imaging infrared rays from a target area where gas possibly leaks, using a capturing condition determined in advance;

generating an image of the target area based on a result of the imaging of the infrared rays;

calculating a reliability degree that indicates whether the capturing condition is suitable for capturing an image of the gas based on peripheral information of the target area and the result of the imaging of the infrared rays, and storing the image of the target area in association with at least one of the reliability degree and the peripheral information; and causing a display device to display a second capturing condition to increase the reliability degree.

18. The image acquisition method according to claim 17, wherein the image of the target area is a heat distribution image;

the calculating comprises calculating the reliability degree for each pixel of the heat distribution image based on peripheral information of the target area and the heat distribution image; and the storing comprises storing the heat distribution image as the image of the target area.

19. A gas imaging device, comprising:

an infrared imager configured to image infrared rays from a target area where gas possibly leaks, using a first capturing condition determined in advance;

a hardware processor configured to generate an image of the target area based on an output result from the infrared imager, and to calculate a reliability degree that indicates whether the first capturing condition is suitable for capturing an image of the gas based on peripheral information of the target area and the output result from the infrared imager and to control a storage device to store the image of the target area in association with at least one of the reliability degree and the peripheral information that includes at least one of wind speed, wind direction, a distance between the infrared imager and the target area, and a vibration state of the infrared imager.

20. The gas imaging device according to claim 19 wherein the peripheral information includes a difference between temperature of the target area and outside air temperature.

21. The gas imaging device according to claim 19, wherein the peripheral information is information input through an input operation by a user.

22. The gas imaging device according to claim 19, wherein the peripheral information is information acquired by a sensor.

23. The gas imaging device according to claim 19, wherein the image of the target area is a heat distribution image; and the hardware processor is configured to calculate the reliability degree for each pixel of the heat distribution image based on peripheral information of the target area and the heat distribution image, and control the storage device to store the heat distribution image as the image of the target area.

* * * * *